United States Patent [19]

Hester, Jr.

[11] Patent Number: 4,479,959
[45] Date of Patent: * Oct. 30, 1984

[54] PROCESS FOR INDUCING HYPNOSIS

[75] Inventor: Jackson B. Hester, Jr., Galesburg, Mich.

[73] Assignee: The Upjohn Company, Kalamazoo, Mich.

[*] Notice: The portion of the term of this patent subsequent to Nov. 15, 2000 has been disclaimed.

[21] Appl. No.: 402,460

[22] Filed: Jul. 28, 1982

Related U.S. Application Data

[63] Continuation of Ser. No. 229,380, Jan. 29, 1981, abandoned, which is a continuation of Ser. No. 125,615, Feb. 28, 1980, abandoned, which is a continuation of Ser. No. 026,938, Apr. 4, 1979, abandoned, which is a continuation of Ser. No. 910,561, May 30, 1978, abandoned, which is a continuation of Ser. No. 821,590, Aug. 4, 1977, abandoned, which is a continuation of Ser. No. 729,295, Oct. 4, 1976, abandoned, which is a continuation of Ser. No. 284,161, Aug. 28, 1972, abandoned.

[51] Int. Cl.$^3$ ............................................. A61K 31/41
[52] U.S. Cl. ..................................................... 424/269
[58] Field of Search ........................................... 424/264

[56] References Cited

U.S. PATENT DOCUMENTS 3,681,343  8/1972  Hester ............................ 260/239.35
3,701,782 10/1972  Hester ............................ 260/239.30

Primary Examiner—Jerome D. Goldberg
Attorney, Agent, or Firm—William G. Jameson; John J. Killinger

[57] ABSTRACT

Therapeutic compositions for treating humans and animals comprising, in dosage unit form, a 8-Chloro-1-hydroxymethyl-6-phenyl-4H-s-triazolo[4,3-a][1,4]benzodiazepine compound of the formula

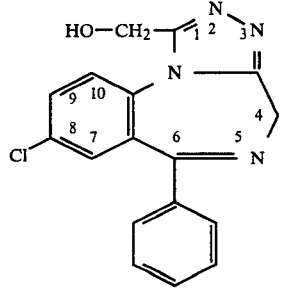

Formula I including the N-oxides, esters, and pharmacologically acceptable acid addition salts thereof in combination with a pharmaceutical carrier. The compositions are useful as soporifics and provide a process for inducing sleep.

4 Claims, No Drawings

PROCESS FOR INDUCING HYPNOSIS

CROSS REFERENCE TO RELATED APPLICATION

This application is a continuation of application Ser. No. 229,380, filed Jan. 29, 1981, now abandoned, which is a continuation of application Ser. No. 125,615, filed Feb. 28, 1980, now abandoned, which is a continuation of application Ser. No. 026,938, filed Apr. 4, 1979, now abandoned, which is a continuation of application Ser. No. 910,561, filed May 30, 1978, now abandoned, which is a continuation of application Ser. No. 821,590, filed Aug. 4, 1977, now abandoned, which in turn is a continuation of application Ser. No. 729,295, filed Oct. 4, 1976, now abandoned, which in turn is a continuation of application Ser. No. 284,161, filed Aug. 28, 1972, now abandoned.

BRIEF SUMMARY OF THE INVENTION

This invention is a therapeutic composition for treating humans and animals comprising a benzodiazepine of the Formula I and including the N-oxides and pharmacologically acceptable acid addition salts thereof in combination with a pharmaceutical carrier and a method for inducing sleep.

DETAILED DESCRIPTION

The compounds of the Formula I can be prepared by methods disclosed in co-pending application Ser. No. 201,207, filed Nov. 22, 1971 now U.S. Pat. No. 3,886,174, and as shown hereafter.

Preparation 8-Chloro-1-(hydroxymethyl)-6-phenyl-4H-s-triazolo[4,3-a][1,4]benzodiazepine A solution of 1,3-dihydro-7-chloro-5-phenyl-2H-1,4-benzodiazepine-2-thione (5.74 g., 0.02 mole) and hydroxyacetic acid hydrazide (4.44 g.) in n-butyl alcohol (300 ml.) was refluxed for about 22 hours with a slow stream of nitrogen bubbling through the reaction mixture for the first hour. The mixture was then cooled and concentrated in vacuo. The resulting residue was suspended in water treated with a little ether and allowed to crystallize. The solid was collected by filtration and dried in vacuo. Recrystallization of this material from methylene chloride-methanol gave 4.06 g. of melting point 203°–205° C., of 8-chloro-1-(hydroxymethyl)-6-phenyl-4H-a-triazolo[4,3-a][1,4]benzodiazepine. The analytical sample recrystallized from ethyl acetate-Skellysolve B had a melting point of 204°–206.5° C.

Anal. calcd. for $C_{17}H_{13}ClN_4O$: C, 62.87; H, 4.03; Cl, 10.92; N, 17.25. Found: C, 62.83; H, 4.24; Cl, 10.93; N, 17.92.

The (5) N-oxides of a compound of the Formula I can be prepared by oxidizing a compound of Formula I with a per-acid such as peracetic, perphthalic, perbenzoic, or m-chloroperbenzoic acid in a solvent that is inert to the oxidation reaction such as a lower alkanol, chloroform, methylene chloride and the like. Preferably the reaction is carried out at a temperature in the range of 0.25° C. The reaction time required will be in the range of 6 to 48 hours.

The oxidation of a compound of the Formula I normally follows a 2-step process with the formation of an oxazirino structure as illustrated below.

The (5) N-oxides of a compound of the Formula I can also be made by reacting a 7-chloro-2-methoxy-5-phenyl-3H-1,4-benzodiazepine 4-oxide with hydroxyacethydrazide. This reaction can be carried out in a solvent inert to the reaction such as a lower alkanol of boiling range of about 100° C. or above, especially 1-butanol or 1-pentanol. It is convenient to reflux the reaction mixture, and a convenient reaction temperature is in the range of 100°–140° C. Under these conditions, the reaction time will be from 12 to 48 hours.

The peracid oxidation method described above for producing the (5) N-oxides of a compound of the Formula I, produces an intermediate oxazirino compound as described above, and this latter compound can be further rearranged to the desired (5) N-oxide by heating in an appropriate solvent inert to the reaction and capable of being sustained in liquid form at normal pressures at temperatures of 150°–200° C. Suitable reaction solvents are the liquid paraffinic hydrocarbons of 10-18 carbon atoms or other solvent hydrocarbons boiling above about 150° C., such as mesitylene. The reaction is conveniently carried out under reflux for 10 minutes to 1 hour.

The above reactions can be shown schematically as follows:

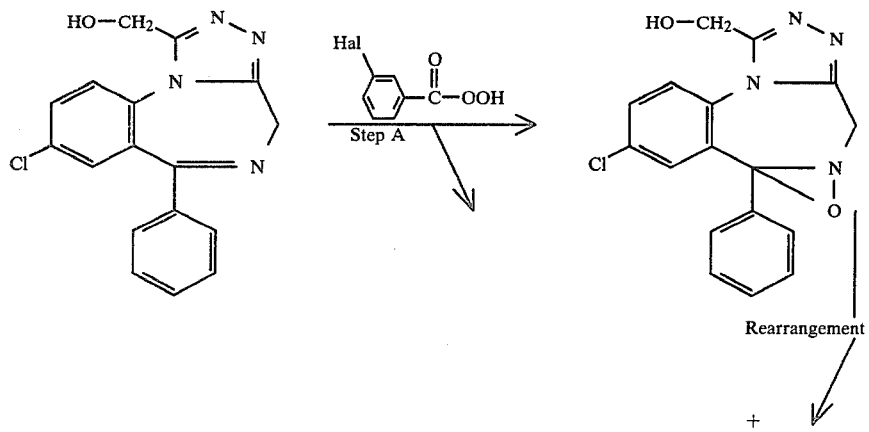

-continued

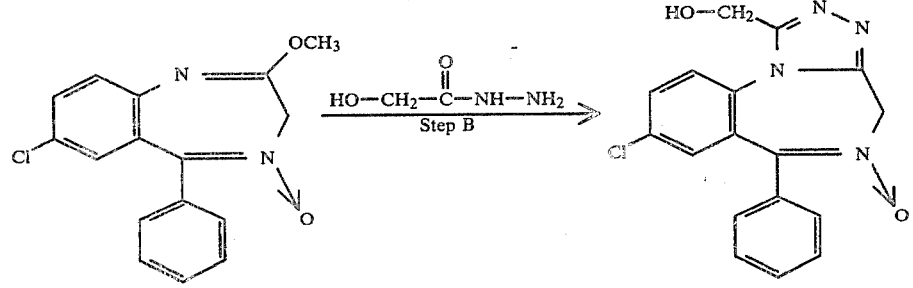

The hydroxy at the 1-hydroxymethyl position can be esterified by general methods for esterification to produce esters, e.g., the acetate hydrogen succinate and the like.

Acid addition salts of compounds of the Formula I can be prepared by neutralization of the free base with the appropriate amount of an inorganic or organic acid, examples of which are hydrochloric, hydrobromic, sulfuric, nitric, phosphoric, acetic, lactic, benzoic, salicyclic, glycolic, succinic, tartaric, maleic, malic, pamoic, cyclohexanesulfamic, citric and methanesulfonic acids, and like acids. The neutralization can be carried out by a variety of procedures known to the art to be generally useful for the preparation of amine acid addition salts. The choice of the most suitable procedure will depend on a variety of factors including convenience of operation, economic considerations, and particularly the solubility characteristics of the particular free base, the acid, and the acid addition salt. If the acid is soluble in water, the free base can be dissolved in water containing an equivalent amount of the acid, and thereafter, the water can be removed by evaporation; in some instances, the salt precipitates from the aqueous solution, particularly when cooled, and evaporation is not necessary. If the acid is soluble in a relatively nonpolar solvent, for example, diethyl ether or diisopropyl ether, separate solutions of the acid and free base in such a solvent can be mixed in equivalent amounts, whereupon the acid addition salt will usually precipitate because of its relatively low solubility in the nonpolar solvent. Alternatively, the free base can be mixed with an equivalent amount of the acid in the presence of a solvent of moderate polarity, for example, a lower alkanol, a lower alkanone, or a lower-alkyl ester of a lower alkanoic acid. Examples of these solvents are ethanol, acetone, and ethyl acetate, respectively. Subsequent admixture of the resulting solution of acid addition salt with a solvent of relatively low polarity, for example, diethyl ether or hexane, will usually cause precipitation of the acid addition salt. These acid addition salts are useful for upgrading the free bases.

The compositions of the present invention are presented for administration to humans and animals in unit dosage forms, such as tablets, capsules, pills, powders, granules, sterile parenteral solutions or suspensions, and oral solutions or suspensions, and oil in water and water in oil emulsions containing suitable quantities of the compound of Formula I.

For oral administration either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Wafers are prepared in the same manner as tablets, differing only in shape and the inclusion of sucrose or other sweetener and flavor. In their simplest embodiment, capsules, like tablets, are prepared by mxing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosages forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent, Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure by ethylene oxide before suspending in the sterile vehicle. Advantageously, a surfactant or wetting agent is included in the composition to facilitate uniform distribution of the compound.

The term unit dosage form as used in the specification and claims refers to physically discrete units suitable as unitary dosages for human subjects and animals, each unit containing a predetermined quantity of active material calculated to produce sleep in association with the required pharmaceutical diluent, carrier, or vehicle. The specifications for the novel unit dosage forms of this invention are dictated by and directly dependent on (a) the unique characteristics of the active material and the particular effect to be achieved, and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, granules, wafers, cachets, teaspoonfuls, tablespoonfuls, dropperfuls, ampuls, vials, segregated multiples of any of the foregoing, and other forms as herein described.

The dosage of the compound for treatment depends on route of administration; the age, weight, and condition of the patient. A dosage schedule of from about 0.5 to 10 mg. in a single dose, embraces the effective range for inducing sleep for which the compositions are effective. The dosage to be administered is calculated on the basis fo from about 0.005 to about 0.2 mg./kg. by weight of subject.

The compound is compounded with a suitable pharmaceutical carrier in unit dosage form for convenient and effective administration. In the preferred embodiments of this invention, the dosage units contain the compound in: 0.5, 1, 5 and 10 mg. amounts for systemic treatment; and 0.1% to 5.0% w/v for parenteral treatment. The dosage of compositions containing a compound of Formula I and one or more other active ingredients is to be determined with reference to the usual dosage of each such ingredient.

In addition to the administration of a compound of Formula I as the principle active ingredient of compositions for treatment of the conditions described herein, the said compound can be combined with other compounds to obtain advantageous combinations of properties. Such combinations include a compound of Formula I with other hypnotics, for example, barbital, 65 to 400 mg.; phenobarbital, 16 to 250 mg.; amobarbital, 65 to 200 mg.; hexobarbital, 250 to 500 mg.; chloral hydrate, 250 to 500 mg.; and methyprylon, 100 to 400 mg.

The following examples are illustrative of the best mode contemplated by the inventor for carrying out his invention and are not to be construed as limiting.

EXAMPLE 1

A lot of 10,000 tablets, each containing 0.5 mg. of 8-chloro-1-hydroxymethyl-6-phenyl-4H-s-triazolo[4,3-a][1,4]-benzodiazepine is prepared from the following types and amounts of ingredients:

| | |
|---|---|
| 8-chloro-1-hydroxymethyl-6-phenyl-4H—s-triazolo[4,3-a][1,4]-benzodiazepine | 5 Gm. |
| Dicalcium phosphate | 1,500 Gm. |
| Methylcellulose, U.S.P. (15 cps.) | 60 Gm. |
| Talc | 150 Gm. |
| Corn Starch | 200 Gm. |
| Calcium stearate | 12 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and stearate, and compressed into tablets.

These tablets are useful in inducing sleep in children at a dose of 1 to 2 tablets at bedtime depending on the age and weight of the patient.

EXAMPLE 2

One thousand two-piece hard gelatin capsules, each containing 0.5 mg. of 8-chloro-1-hydroxymethyl-6-phenyl-4H-s-triazolo[4,3-a][1,4]benzodiazepine are prepared from the following types and amounts of ingredients:

| | |
|---|---|
| 8-chloro-1-hydroxymethyl-6-phenyl-4H—s-triazolo[4,3-a][1,4]benzodiazepine | 0.5 Gm. |
| Talc | 25 Gm. |
| Lactose | 250 Gm. |

The ingredients are mixed well and filled into capsules of the proper size.

Capsules so prepared are useful to produce sleep at a dose of one capsule at bedtime.

EXAMPLE 3

One thousand tablets for sublingual use are prepared from the following ingredients:

| | |
|---|---|
| 8-chloro-1-hydroxymethyl-6-phenyl-4H—s-triazolo[4,3-a][1,4]benzodiazepine | 5 Gm. |
| Polyethylene glycol 4,000, powdered | 150 Gm. |
| Polyethylene glycol 6,000, powdered | 75 Gm. |

The ingredients are mixed well and compressed into sublingual-type tablets weighing 230 mg.

These tablets placed under the tongue are useful in the rapid induction of sleep at a dose of 1 tablet at bedtime.

EXAMPLE 4

Soft gelatin capsules for oral use, each containing 1 mg. of 8-chloro-1-hydroxymethyl-6-phenyl-4H-s-triazolo-[4,3-a][1,4]benzodiazepine are prepared by first dispersing the micronized compound in corn oil to render the material capsulatable and then encapsulating in the usual manner.

One capsule taken at bedtime is useful to produce sleep.

EXAMPLE 5

One thousand tablets, each containing 5 mg. of 8-chloro-1-hydroxymethyl-6-phenyl-4H-s-triazolo[4,3-a][1,4]benzodiazepine are made from the following types and amounts of ingredients:

| | |
|---|---|
| 8-chloro-1-hydroxymethyl-6-phenyl-4H—s-triazolo[4,3-a][1,4]benzodiazepine | 5 Gm. |
| Lactose | 355 Gm. |
| Microcrystalline cellulose NF | 120 Gm. |
| Starch | 16 Gm. |
| Magnesium stearate powder | 4 Gm. |

The ingredients are screened and blended together and pressed into 500 mg. tablets.

The tablets are useful to produce sleep.

EXAMPLE 6

A sterile preparation suitable for intramuscular injection and containing 1 mg. of 8-chloro-1-hydroxymethyl-6-phenyl-4H-s-triazolo[4,3-a][1,4]-benzodiazepine in each milliliter is prepared from the following ingredients:

| 8-chloro-1-hydroxymethyl-6-phenyl-4H—s-triazolo[4,3-a][1,4]benzo-diazepine | 1 Gm. |
|---|---|
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected to produce sleep.

I claim:

1. A process for inducing sleep comprising the administration to a human or animal subject in need of sleep, in unit dosage form from about 0.005 mg. to about 0.2 mg./kg. body weight of 8-chloro-1-hydroxymethyl-6-phenyl-4H-s-triazolo[4,3-a][1,4]-benzodiazepine or a pharmacologically acceptable acid addition salt acetate or hydrogen succinate, ester, or (5) N-oxide thereof in association with a pharmaceutical carrier.

2. The process of claim 1 wherein the 8-chloro-1-hydroxymethyl-6-phenyl-4H-s-triazolo[4,3-a][1,4]benzodaizepine is in the form of the hydrobromic acid addition salt.

3. The process of claim 1 wherein the 8-chloro-1-hydroxymethyl-6-phenyl-4H-s-triazolo[4,3-a][1,4]benzodiazepine is in the form of the (5) N-oxide.

4. The process of claim 1 wherein the 8-chloro-1-hydroxymethyl-6-phenyl-4H-s-triazolo[4,3-a][1,4]benzodiazepine is in the form of the free base.

* * * * *